United States Patent [19]

Blake, III

[11] Patent Number: 5,273,542

[45] Date of Patent: Dec. 28, 1993

[54] PRE-FILLED SYRINGE WITH FLOW VALVE

[75] Inventor: Joseph W. Blake, III, New Canaan, Conn.

[73] Assignee: The Medtech Group, Inc., South Plainfield, N.J.

[21] Appl. No.: 944,455

[22] Filed: Sep. 14, 1992

[51] Int. Cl.$^5$ ............................................. A61M 5/00
[52] U.S. Cl. ..................................... 604/110; 604/238
[58] Field of Search ................ 604/110, 187, 238, 195

[56] References Cited

U.S. PATENT DOCUMENTS

| | | | |
|---|---|---|---|
| 2,893,390 | 7/1959 | Lockhart | 604/238 |
| 3,941,128 | 3/1976 | Baldwin | 604/238 |
| 4,479,801 | 10/1984 | Cohen | 604/238 |
| 4,932,939 | 6/1990 | Magre et al. | 604/195 X |

Primary Examiner—John D. Yasko
Attorney, Agent, or Firm—Arthur L. Plevy

[57] ABSTRACT

The present invention is a hypodermic syringe pre-filled with a volume of a desired solution. A plug member is positioned within the hypodermic syringe in between the pre-filled fluid and the lumen of the syringe's cannula. The presence of the plug member within the hypodermic syringe separates the cannula from the pre-filled fluid thereby leaving the cannula unaffected by the presence of the fluid within the syringe. As the plunger of the hypodermic syringe is engaged, the pressure of the pre-filled fluid is increased. The fluid pressure acts upon the plug member, displacing the plug member when a predetermined fluid pressure is achieved. Once the plug member is displaced, the occlusion between the pre-filled fluid and the cannula is removed and the pre-filled fluid is free to flow through the lumen of the cannula.

17 Claims, 4 Drawing Sheets

PRE-FILLED SYRINGE WITH FLOW VALVE

FIELD OF THE INVENTION

The present invention relates to a disposable hypodermic syringe pre-filled with a volume of a desired liquid and more particularly to such pre-filled hypodermic syringes that include a valving means that prevents the liquid contained within the syringe from inadvertently flowing out of the cannula of the syringe prior to use.

BACKGROUND OF THE INVENTION

Pre-filled hypodermic syringes provide an exact dose of a desired medication or other fluid ready for immediate use. Consequently, there exist many situations where pre-filled hypodermic syringes are preferable over conventional syringes that are filled when needed. One advantage of pre-filled hypodermic syringes is that the dosage of medication or fluid contained within the syringe is factory controlled. As such, variations in mixture concentrations or dosages that can occur each time an empty syringe is manually filled can be eliminated. Additionally, by pre-filling a syringe at the point of manufacture, the needle of the pre-filled syringe can remain sterile until its moment of use. With conventional empty syringes the syringe must be handled as fluid is drawn into the syringe, thereby resulting in the increased risks of contaminating either the fluid and/or the needle of the syringe.

One of the largest advantages of the pre-filled hypodermic syringes is that of convenience. Pre-filled hypodermic syringes eliminate the need to fill conventional empty syringes from vials, thereby saving both time and labor. Furthermore, the use of pre-filled hypodermic syringes enables people unskilled in mixing solutions and filling syringes to properly administer intravenous injections. As a result of the ease of using pre-filled hypodermic syringes, pre-filled hypodermic syringes have become commonplace for use in high volume situations. For instance, pre-filled hypodermic syringes are commonly used during immunization programs where exacting dosages of vaccine are administered to a large number of people by only a few attending medical personnel. Similarly, pre-filled syringes are commonly used by people who require repeat self-administered injections such as diabetics and hemophiliacs. The use of pre-filled syringes provides such persons with the convenience of not having to fill a syringe each time an injection is required. Furthermore, pre-filled hypodermic syringes permit an untrained person to administer a proper dosage of medication to a person, such as a diabetic, should that person be unable to administer such an injection him or herself.

Conventional hypodermic syringes, be they pre-filled or not, work essentially in the same manner. The syringe contains a fluid reservoir coupled to a hollow cannula. By engaging the plunger of the hypodermic syringe, the volume of the fluid reservoir can be changed and fluid can be either discharged from, or drawn into, the syringe through the lumen of the cannula. In pre-filled syringes, the syringe plunger is drawn to a preset position thereby retaining a desired volume of fluid within the syringe. The lumen of the cannula is selectively blocked, thereby preventing the desired volume of fluid within the syringe from changing. In conventional prior art pre-filled hypodermic syringes, the lumen of the cannula is blocked by positioning the sharpened point of the cannula within an elastomeric stopper. The elastomeric stopper envelops the sharpened point of the cannula in a fluid impervious manner thereby preventing the flow of fluid out of the syringe through the cannula. Such elastomeric stoppers are often formed as part of the protective sheathing for the syringe cannula as exemplified by copending U.S. patent application Ser. No. 07/804,091 entitled DISPOSABLE PRE-FILLED SYRINGE WITH RETRACTABLE NEEDLE and assigned to Medtech Group, Inc. to assignee herein.

The use of elastomeric stoppers is commonplace because they are effective, easy to use and inexpensive to manufacture. However, in certain situations elastomeric stoppers do have disadvantages. Since elastomeric stoppers block the lumen of a syringes cannula at its sharpened point, the fluid contained within the syringe also fills the lumen of the cannula leading to the elastomeric stopper. In many hypodermic syringes the lumen within the cannula is extremely narrow. As such, with certain solutions, the presence of the fluid within the confined space of the cannula lumen promotes crystallization. The resulting crystallization could then obstruct the lumen.

It is therefore a primary objective of the present invention to provide a pre-filled syringe wherein the fluid within the syringe is held in a manner that prevents the loss of fluid prior to use, and similarly does not permit the retained fluid to enter the cannula of the syringe until the syringe is enabled and readied for use.

SUMMARY OF THE INVENTION

The present invention is a hypodermic syringe pre-filled with a volume of a desired solution. A plug member is positioned within the hypodermic syringe in between the pre-filled fluid and the lumen of the syringe's cannula. The presence of the plug member within the hypodermic syringe separates the cannula from the pre-filled fluid thereby leaving the cannula unaffected by the presence of the fluid within the syringe. As the plunger of the hypodermic syringe is engaged, the pressure of the pre-filled fluid is increased. The fluid pressure acts upon the plug member, displacing the plug member when a predetermined fluid pressure is achieved. Once the plug member is displaced, the occlusion between the pre-filled and the cannula is removed and the pre-filled fluid is free to flow through the lumen of the cannula.

In a preferred embodiment, the plug member is an elastomeric ball which is positioned in a narrow region of the syringe barrel proximate the cannula. The diameter of the elastomeric ball is larger than the diameter of the narrow region, as such the elastomeric ball is deformed and positioned within the narrow region with an interference fit. An enlarged region is formed between the narrow region and the cannula. As the fluid is compressed to the predetermined pressure, the fluid pressure forces the elastomeric ball to traverse the narrow region and enter the enlarged region. The enlarged region is larger then the elastomeric ball, consequently, the elastomeric ball is free moving within the enlarged area and the fluid can flow past the elastomeric ball and out of the cannula. To help retain the elastomeric ball within the narrow region before the predetermined fluid pressure is reached, an annular protrusion is formed between the narrow region and the enlarged region. The aperture through the annular protrusion is smaller then the diameter of the elastomeric ball. As such, the annular protrusion helps retain the elastomeric ball until the fluid pressure forces the elastomeric ball to deform through the aperture of the annular protrusion and into the enlarged region.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the features of the present invention pre-filled syringe can be adapted to many differing hypodermic syringe designs, it is especially suited for use in connection with hypodermic syringes that have either removable needle assemblies or retractable needle assemblies. Accordingly, the present invention will be described in connection with three exemplary embodiments of a hypodermic syringe, one showing a retractable needle assembly and two showing a removable needle assembly.

Figure 1:
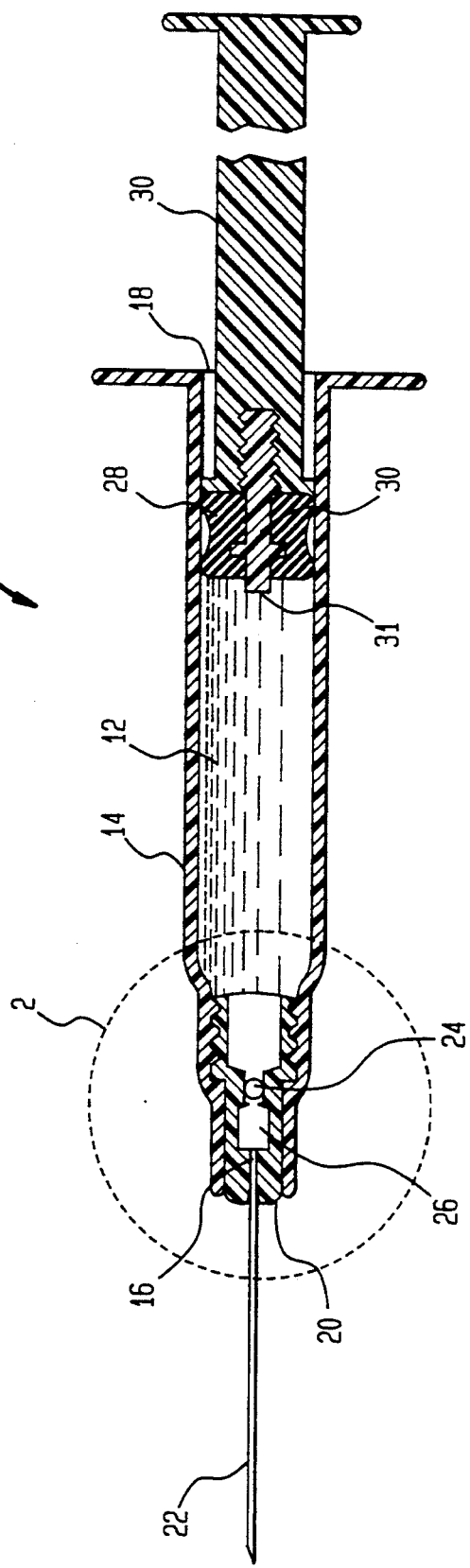
FIG. 1 is a cross-sectional view of one preferred embodiment of the present invention hypodermic syringe.

Referring to FIG. 1, one preferred embodiment of the present invention pre-filled hypodermic syringe 10 is shown in an unused condition wherein the syringe 10 is filled with a given volume of a desired fluid 12. The syringe 10 is defined by a hollow syringe barrel 14 having an open distal end 16 and an open proximal end 18. The distal end 16 of the syringe barrel 14 is occluded by the presence of a retractable cannula base 20, which in the shown embodiment threadably engages the distal end 16 of the syringe barrel 14. The retractable cannula base 20 supports a pointed cannula 22, wherein the lumen of the cannula 22 provides the only exit through which the fluid 12 within the syringe 10 may be discharged. The flow of fluid 12 from the syringe barrel 14 to the lumen of the cannula 22 is blocked by the presence of an elastomeric ball 24. The presence of the elastomeric ball 24 within the retractable cannula base 20 creates a liquid impervious occlusion that prevents the fluid 12 from reaching the cannula 22. As such, prior to the use of the pre-filled syringe 10, an open region 26 proximate the cannula 22 and within the retractable cannula base 20, is dry and is unaffected by the presence of fluid 12 on the other side of the elastomeric ball 24.

An elastomeric grommet 28, supported by a plunger 30 and plunger rod 33 prevents the fluid 12 within the syringe barrel 14 from flowing out the open proximal end 18 of the syringe barrel 14. Extending into the syringe barrel 14 beyond the elastomeric grommet is a male connector 31 which is used to engage and retract the retractable cannula base 20. The shape, function and method by which the male connector 31 engages and retracts the retractable cannula base 20 is described in U.S. Pat. No. 5,171,300 issued Jan. 22, 1991 and entitled DISPOSABLE HYPODERMIC SYRINGE which is herein incorporated by reference.

Figure 2:
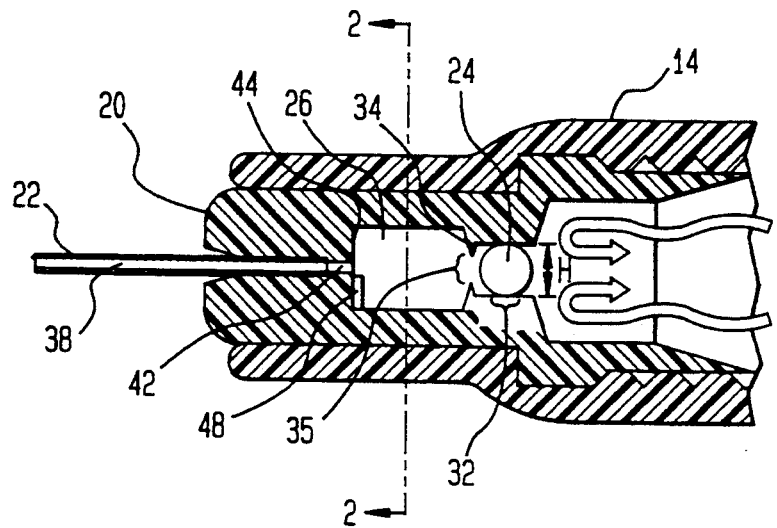
FIG. 2 is an enlarged, selectively cross-sectional view of a segment of the present invention hypodermic syringe contained with the circled region of FIG. 1, as it would appear prior to use.

Referring now to FIG. 2 it can be seen that the open region 26 proximate the cannula 22, within the retractable cannula base 20, is larger than the size of the elastomeric ball 24. The elastomeric ball 24 itself is positioned in a narrowed region 32 that has a height H that is slightly smaller than the diameter of the elastomeric ball 24. As such, when the elastomeric ball 24 is positioned within the narrowed region 32, the elastomeric ball 24 is slightly compressed by the walls of the narrowed region 32, thereby creating an interference fit and a fluid impervious seal. An annular protrusion 34 is formed within said retractable cannula base 20 in between the open region 26 and the narrow region 32. The annular protrusion 34 extends inwardly, consequently the aperture 35 formed by the annular protrusion 34 has a diameter that is smaller than both the diameter of the narrow region 32 and the diameter of the open region 26. Since the annular protrusion 34 is positioned in between the narrow regions 32 and the open region 26, the elastomeric ball 24 abuts against the stopping protrusion 34 as the elastomeric ball 24 is biased toward the open region 26 by the hydraulic forces within the syringe barrel 14. As such, the presence of the annular protrusion 34 prevents the elastomeric ball 24 from being displaced into the open region 26. In the opposite direction, the elastomeric ball 24 is prevented from falling into the syringe barrel 14 by the interference fit of the elastomeric ball 24 within the confines of the narrow region 32.

FIG. 2 shows the position of the elastomeric ball 24 within the retractable cannula base 20 as it would appear prior to the use of the pre-filled syringe 10. At this position the open chamber 26 and the interconnecting lumen 38 of the cannula 22 are isolated from the retained fluid 12 by the elastomeric ball 34. As the pre-filled syringe 10 is packaged, shipped and handled, the syringe 10 may incur inadvertent manipulations that result in an increase of pressure within the retained fluid 12. Similarly, many pre-filled syringes come with detached plunger rods 33. Consequently, prior to the use of the syringe 10, the plunger rod 33 has to be attached to the plunger 30 within the syringe barrel 14. The attachment of the plunger rod 33 to the syringe 10 often results in inadvertent forces being applied to the plunger 30 that increases the pressure of the retained fluid. As the pressure of the retained fluid 12 within the syringe 10 increases, the pressure differential between the open chamber 26 on one side of the elastomeric ball 24 and the fluid 12 on the other side of the elastomeric ball 24 increases. Consequently, the elastomeric ball 24 is driven toward the open region 26 by the pressure differential. As the elastomeric ball 24 is forced toward the open region 26 of the retractable cannula base 20, the elastomeric ball 24 contacts the annular protrusion 34 which extends inwardly from the retractable cannula base 20 in between the narrow region 32 retaining the elastomeric ball 24 and the open region 26. In order to surpass the annular protrusion 34, the elastomeric ball 24 must deform through the narrow aperture 35 defined by the annular protrusion 34. The force differential needed between the open region 26 and the fluid 12 in order to deform the elastomeric ball 24 through the aperture 35 of the annular protrusion 34 requires a predetermined minimum fluid pressure to be achieved within the syringe barrel 14. The pressure of the fluid 12 within the syringe barrel 14 is governed by the reciprocal position of the plunger 30 within the syringe barrel 14. Consequently, in order to deform the elastomeric ball 24 through the aperture 35 of the annular protrusion 34, the plunger 30 must be advanced within the syringe barrel 14 a predetermined distance. Furthermore, as the plunger 30 is advanced, and before the elastomeric ball 24 is driven past the annular protrusion 34, the pressure of the fluid 12 within the syringe barrel 14 opposes the advancement of the plunger 30. Consequently, in order to drive the elastomeric ball 24 past the stopping protrusion 34, the plunger 30 must be engaged with a predetermined force large enough to compress the fluid 12 to a pressure that is significant enough to displace the elastomeric ball 24 through past the annular protrusion 34.

The force required to displace the elastomeric ball 24 through the aperture 35 of the annular protrusion 36 and into the open region 26 is much greater than the inadvertent forces the syringe 10 typically receives during the attachment of the plunder rod 33 to the plunger 30 and during packing, shipping and handling. Consequently, the need for deforming the elastomeric ball 24 through the annular protrusion 36 prevents the present invention pre-filled syringe 10 from being inadvertently enabled prior to actual use.

Figure 3:
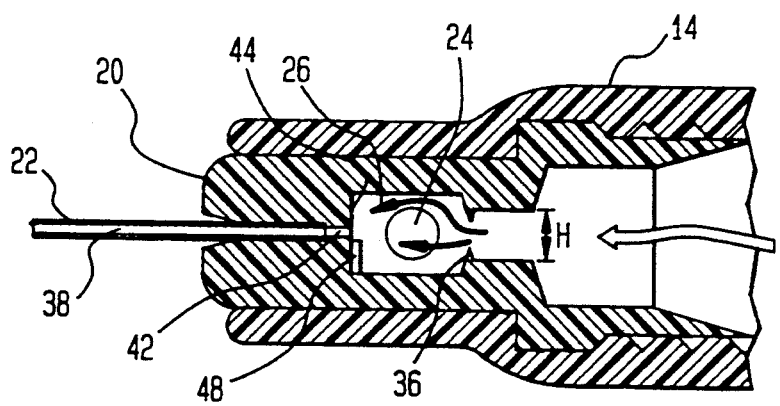
FIG. 3 shows the embodiment of FIG. 2, as it would appear during the use of the present invention hypodermic syringe.

Referring to FIG. 3 it can be seen that when the pressure differential between the fluid 12 and the open region 26 is exceeds the predetermined minimum value, the elastomeric ball 24 deforms past the annular protrusion 34 and enters the open region 26. As such, the elastomeric ball 24 no longer acts as an occlusion and the fluid 12 within the syringe barrel 14 can flow past the narrow region 32 of the retractable cannula base 20, through the aperture 35 of the annular protrusion 34 and into the open region 26.

Figure 4:
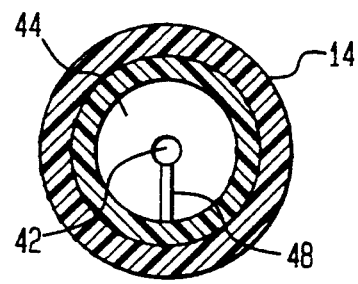
FIG. 4 shows a cross-sectional view of the embodiment of FIG. 2, viewed along section line 4—4.
Figure 5:
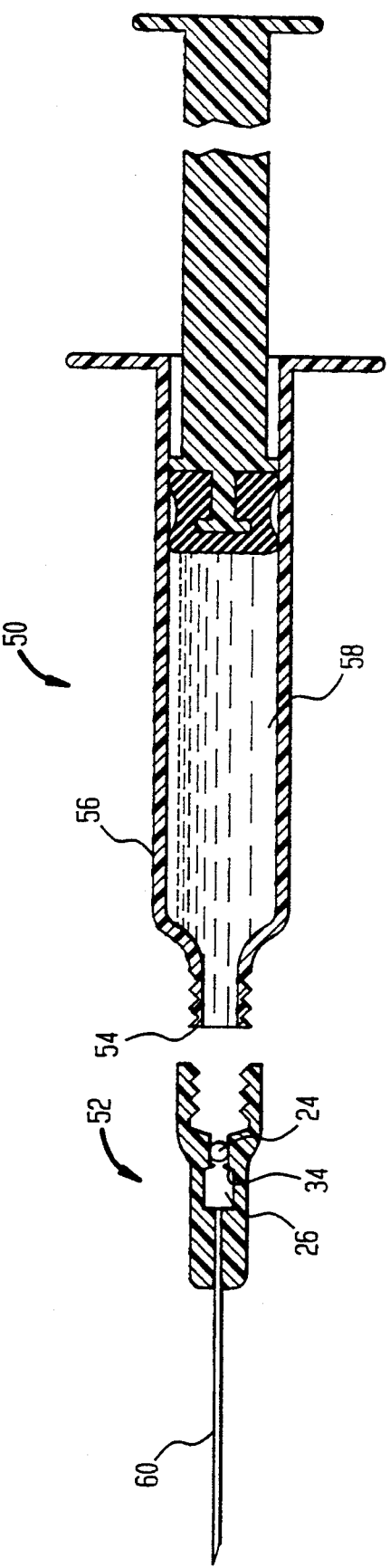
FIG. 5 is a cross-sectional view of a second preferred embodiment of the present invention hypodermic syringe.

As has been previously mentioned, the open region 26 of the retractable cannula base 20 is larger than the elastomeric ball 24. As such, the elastomeric ball 24 becomes free moving as the elastomeric ball 24 is displaced into the open region 26. The lumen 38 of the cannula 22 is coupled to the open region 26 of the retractable cannula base 20 via a small flow orifice 42. Referring now to FIG. 5 in conjunction with FIG. 4, it can be seen that the flow orifice 42 is centrally positioned on the distal wall 44 of the open region 26. A non-symmetrical rib 48 is formed on the distal wall 44 of the open region 26, adjacent the flow orifice 42. The presence of the rib 48 prevents the elastomeric ball 24 from blocking the flow orifice 42 and occluding the flow of fluid 12 into the lumen 38 of the cannula 22. With the elastomeric ball 24 positioned within the open region 26 of the retractable cannula base 20, room exists around the elastomeric ball 24 through which the fluid 12 may flow. Consequently, as the plunger 30 is advanced within the syringe barrel 14, the pre-filled fluid 12 is displaced through the retractable cannula base 20, past the elastomeric ball 24 and into the cannula 22. As such, it can be seen that the fluid 12 pre-filled within the syringe 14 does not contact the cannula 22 until the elastomeric ball 24 is purposely displaced into the open chamber 26 of the retractable cannula base 20 just prior to use, thereby avoiding the prior art disadvantage of the fluid 12 laying stagnant and crystallizing within the cannula 20.

It should be understood that the use of an elastomeric ball in the above described embodiment is merely exemplary and other shapes and materials may be used. For example, instead of an elastomeric ball, a stainless steel or glass ball may be used. If such a construction was chosen, a stainless steel or glass ball would not deform at a predetermined pressure, rather the ball would cause the annular protrusion 34 to deform as the ball was forced through the aperture 35 of the annular protrusion 34. Similarly, a non-spherical plug could be used in place and stead of the described elastomeric ball, provided the plug is capable of being displaced past the stopping protrusion 34 and into the open region 26 of the retractable cannula base 20 by the force of the fluid pressure in the syringe barrel 14.

In the exemplary embodiment of the present invention illustrated by the figures, the pre-filled syringe 10 is of a construction that allows the cannula 22 to be retracted into the syringe barrel 14. Syringes with retractable needle assemblies are one preferred embodiment for the present invention because such syringes often include separately formed needle assembles and syringe barrels. Since the present invention syringe requires the positioning of an open region 26, annular protrusion 32 and the placement of the elastomeric ball 24 proximate the cannula, it should be recognized that such this construction is more readily manufactured into a separate needle assembly, that can be later attached to a syringe barrel, than to a unistructurally formed syringe barrel with needle. As such, it should be understood that although the present invention syringe can be formed into any known syringe construction, syringe constructions with separately formed needle assemblies are preferred.

Referring now to FIG. 5, an alternative embodiment of the present invention pre-filled syringe 50 is shown. In this embodiment, the needle assembly 52 is not retractable. Rather, the needle assembly 52 is removably attachable to the distal end 54 of the syringe barrel 56. Needle assemblies that threadably engage the distal ends of syringes are a well known and practiced art. However, in the shown embodiment of the present invention syringe 50, the needle assembly 52 is formed to include the elastomeric ball 24, annular protrusion 34 and open region 26 previously described. As such, the fluid 58 contained within the syringe barrel 56 is isolated from the cannula 60 by the presence of the elastomeric ball 24 in the needle assembly 52 until the elastomeric ball 24 is displaced into the open region 26 in the manner previously described in association with the first exemplary embodiment.

Figure 6:
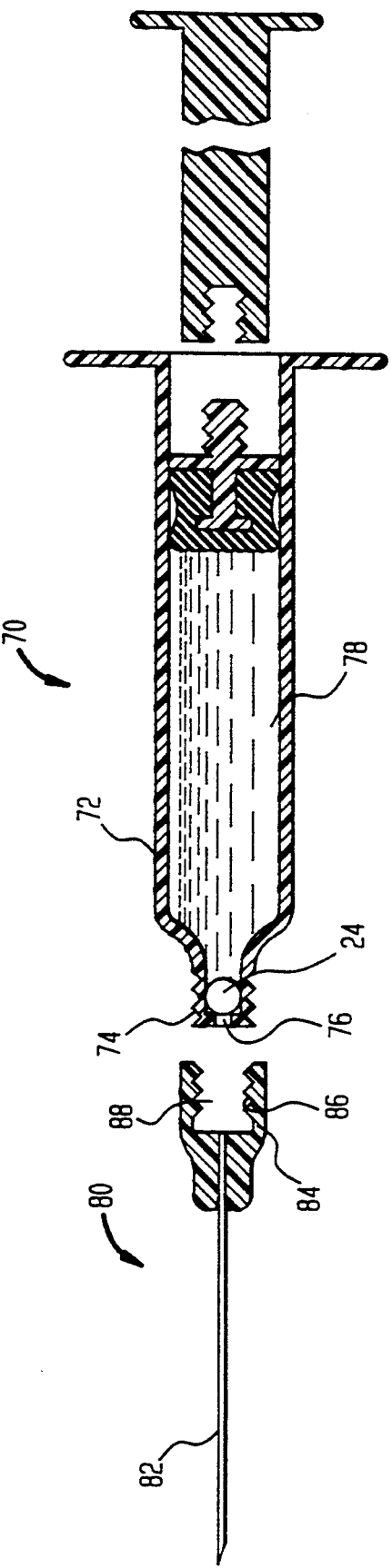
FIG. 6 is a cross-sectional view of a third preferred embodiment of the present invention hypodermic syringe.

In FIG. 6, a second alternative embodiment of the present invention pre-filled syringe 70 is shown. In this embodiment, the syringe barrel 72 has a tapered neck 74 which is externally threaded. Within the tapered neck 74 is positioned the elastomeric ball 24. The elastomeric ball 24 is sized to have a diameter slightly larger than the diameter of the lumen within the tapered neck 74. Consequently, an interference fit exists between the elastomeric ball 24 and the tapered neck 74 that retains the elastomeric ball 24 within the tapered neck 74 and creates a fluid impervious occlusion. At the distal end of the tapered neck 74, is molded an annular protrusion 76. The annular protrusion 76 extends inwardly toward the lumen of the tapered neck 74, as such the elastomeric ball 24 abuts against the annular protrusion 76 as the pressure of the fluid 78 within the syringe barrel 72 increases.

The tapered neck 74 of the syringe barrel 72 threadably engages a needle assembly 80. The needle assembly 80 is comprised of a cannula 82 and a needle base 84. The needle base 84 is largely hollow having an internally threaded region 86 that leads into an open region 88 proximate the cannula 82. As the needle assembly 80 is threadably engaged by the tapered neck 74 of the syringe barrel 72, the open region 88 within the needle base 80 is positioned adjacent to the open region 88. As such, fluid 78 contained within the syringe barrel 72 is isolated from both the open region 88 and the cannula 82 by the presence of the elastomeric ball 24 within the syringe neck. To enable the syringe 70, the pressure of the fluid 78 within the syringe barrel 72 is increased until the elastomeric ball 24 is displaced past the cannula protrusion 76 and into the open region 88 so as to operate in the manner previously described in association with the previous embodiments.

It will be understood that the embodiments described herein are merely exemplary and that a person skilled in the art may make many variations and modifications to the described embodiments utilizing functionally equivalent elements to those described. More specifically, it should be understood that any shaped and constructed plug can be used in place and stead of the elastomeric ball described. Additionally, dimensions and proportions of interrelating parts can be altered to effect the forces needed to enable the pre-filled syringe. All such variations and modifications are intended to be included within the scope of this invention as defined by the append claims.

What is claimed is:

1. A hypodermic syringe comprising:
   a syringe barrel, pre-filled with a desired fluid, having a distal end and a constricted region of a predetermined diameter proximate said distal end;
   a cannula means coupled to said distal end of said syringe barrel;
   a plunger means for displacing said fluid out of said syringe barrel, past said constricted region and through said cannula means;
   a stopper element disposed within said constricted region, wherein said stopper element is retained within said constricted region with an interference fit thereby, creating a fluid impervious seal within said constricted region that prevents the flow of said fluid to said cannula means;
   at least one projection extending inwardly from said constricted region defining a reduced area within said constricted region, wherein said reduced area is smaller than said stopper element and prevents said stopper element from being displaced out of said constricted region until said stopper element is forced through said reduced area by a predetermined force applied to said fluid by said plunger means.

2. The hypodermic syringe according to claim 1, wherein said stopper element prevents said fluid from contacting said cannula means prior to the application of said predetermined force to said plunger means.

3. The hypodermic syringe according to claim 1, wherein said stopper element is formed from an elastomeric material, enabling said stopper element to deform through said reduced area as said stopper element is displaced by said fluid as said predetermined force is applied to said plunger means.

4. The hypodermic syringe according to claim 1, wherein said stopper element deforms said at least one projection defining said reduced area as said stopper element is displaced through said reduced area by said fluid as said predetermined force is applied to said plunger means.

5. The hypodermic syringe according to claim 1 further including a means for selectively retracting said cannula means into said syringe barrel.

6. The hypodermic syringe according to claim 1, wherein an enlarged region is positioned between said constricted region and said cannula means, said stopper element being displaced through said reduced area of said constricted region into said enlarged region as said predetermined force is applied to said plunger means, wherein said fluid flows through said constricted region and past said stopper element in said enlarged region to reach said cannula means.

7. The hypodermic syringe according to claim 6, further including a means for preventing said stopper element from obstructing the flow of said fluid into said cannula means when said stopper element is within said enlarged region.

8. The hypodermic syringe according to claim 1, wherein said at least one projection includes an annular protrusion that extends inwardly from said constricted region, wherein said annular protrusion defines a reduced area having a diameter that is smaller than said predetermined diameter of said constricted area.

9. The hypodermic syringe according to claim 1, wherein said stopper element is generally spherical in shape.

10. The hypodermic syringe according to claim 4, wherein said stopper element is metal.

11. The hypodermic syringe according to claim 4, wherein said stopper element is plastic.

12. A hypodermic syringe, comprising:
    a syringe barrel having a distal end, wherein said syringe barrel is pre-filled with a desired fluid;
    a retractable needle assembly coupled to said distal end of said syringe barrel, wherein said retractable needle assembly includes a cannula and a fluid conduit that leads to said cannula;
    a plunger for displacing said fluid from said syringe barrel past said fluid conduit and out said cannula of said retractable needle assembly;
    a stopper element disposed within said fluid conduit, wherein said stopper element is retained within said fluid conduit with an interference fit, thereby creating a fluid impervious seal within said fluid conduit and preventing the flow of said fluid through said cannula;
    at least one projection extending inwardly from said fluid conduit defining a reduced area within said fluid conduit, wherein said reduced area is smaller than said stopper element and prevents said stopper element from being displaced from said fluid conduit until said stopper element is forced through said reduced area by a predetermined force applied to said fluid by said plunger means.

13. The hypodermic syringe to claim 12, wherein said stopper element is formed from an elastomeric material, enabling said stopper element to deform through said reduced area as said stopper element is displaced from said fluid conduit by said fluid when said predetermined force is applied to said plunger means.

14. The hypodermic syringe according to claim 12, wherein said stopper element deforms said at least one projection extending inwardly from said fluid conduit as said stopper element is displaced out of said fluid conduit, past said at least one projection, by said fluid as said predetermined force is applied to said plunger means.

15. The hypodermic syringe according to claim 12, wherein an enlarged region is disposed between said reduced area of said fluid conduit and said cannula, said stopper element being displaced past said reduced area into said enlarged region as said predetermined force is applied to said fluid by said plunger means, whereby fluid flows through said fluid conduit and past said stopper element in said enlarged region to reach said cannula.

16. The hypodermic syringe according to claim 15, further including a means for preventing said stopper element from obstructing the flow of said fluid to said cannula when said stopper element is within said enlarged region.

17. The hypodermic syringe according to claim 12, wherein said at least one projection is an annular protrusion that extends inwardly from said fluid conduit, wherein said annular protrusion defines a reduced area having a predetermined diameter.

* * * * *